United States Patent
Patil et al.

(10) Patent No.: US 11,850,224 B2
(45) Date of Patent: *Dec. 26, 2023

(54) STORAGE STABLE AQUEOUS INJECTABLE SOLUTION COMPRISING DICLOFENAC

(71) Applicant: R K PHARMA INC, Pearl River, NY (US)

(72) Inventors: Sushilkumar Dhanaji Patil, Gujarat (IN); Nirav Ishwarlal Khatri, Gujarat (IN); Alex Kochukunju George, Gujarat (IN); Sushrut Krishnaji Kulkarni, Gujarat (IN)

(73) Assignee: RK PHARMA INC., Pearl River, NY (US)

( * ) Notice: Subject to any disclaimer, the term of this patent is extended or adjusted under 35 U.S.C. 154(b) by 140 days.

This patent is subject to a terminal disclaimer.

(21) Appl. No.: 17/405,292

(22) Filed: Aug. 18, 2021

(65) Prior Publication Data

US 2021/0369659 A1 Dec. 2, 2021

Related U.S. Application Data

(63) Continuation of application No. 15/933,937, filed on Mar. 23, 2018, now Pat. No. 11,110,073.

(30) Foreign Application Priority Data

Mar. 24, 2017 (IN) .............................. 201721010402

(51) Int. Cl.
| | | |
|---|---|---|
| *A61K 31/196* | (2006.01) | |
| *A61K 9/00* | (2006.01) | |
| *A61K 45/06* | (2006.01) | |
| *A61K 47/32* | (2006.01) | |
| *A61K 9/08* | (2006.01) | |

(52) U.S. Cl.
CPC .......... *A61K 31/196* (2013.01); *A61K 9/0019* (2013.01); *A61K 9/08* (2013.01); *A61K 45/06* (2013.01); *A61K 47/32* (2013.01)

(58) Field of Classification Search
CPC ........ A61K 31/196; A61K 47/32; A61K 9/08; A61K 9/0019
See application file for complete search history.

(56) References Cited

U.S. PATENT DOCUMENTS 11,110,073 B2 * 9/2021 Patil .................... A61K 9/08

FOREIGN PATENT DOCUMENTS

WO WO-2016170401 A1 * 10/2016 ........... A61K 31/196

* cited by examiner

*Primary Examiner* — James D. Anderson
(74) *Attorney, Agent, or Firm* — Ladas & Parry LLP

(57) ABSTRACT

The present invention relates to a stable, aqueous, injectable solution comprising diclofenac and polyvinylpyrrolidone. The present invention also relates to processes for preparing the injectable solution.

2 Claims, No Drawings

STORAGE STABLE AQUEOUS INJECTABLE SOLUTION COMPRISING DICLOFENAC

RELATED APPLICATION

This application is a CONTINUATION of application Ser. No. 15/933,937 filed on Mar. 23, 2018, which claims priority from Indian Patent Application No. 201721010402 filed on Mar. 24, 2017, the disclosures of which is incorporated in its entirety by reference herein.

FIELD OF THE INVENTION

The field of the present invention relates to a stable, aqueous, injectable solution comprising diclofenac and polyvinylpyrrolidone. The present invention also relates to processes for preparing the injectable solution.

BACKGROUND OF THE INVENTION

Diclofenac is widely prescribed analgesic and anti-inflammatory agent and may be administered via oral as well as parenteral route. Oral dose of diclofenac ranges from 100 mg to 200 mg per day, while parenteral dose ranges from 75 to 150 mg per day.

U.S. Pat. No. 5,389,681 discloses sterilizable parenteral solution comprising a diclofenac salt, solubilisers such as 1,2-propylene glycol or polyethylene glycol 300-400, stabilisers such as glutathione or N-acetyl cysteine and a carrier liquid, such as water.

Indian Application No. 1382/MUM/2008 discloses injectable composition comprising diclofenac, polyoxyl 35 castor oil, benzyl alcohol, sodium sulphite, disodium EDTA and water as a principal solvent.

U.S. Publication No. 2012/0142779 discloses parenteral aqueous solution comprising either (a) diclofenac or a pharmaceutically acceptable diclofenac salt and a cyclodextrin, or (b) an inclusion complex of diclofenac or a pharmaceutically acceptable diclofenac salt and a cyclodextrin, or a mixture of both.

Indian Application No. 1438/MUM/2012 discloses injectable composition comprising diclofenac and/or its acceptable salts, macrogol 15 hydroxystearate and pharmaceutically acceptable excipients.

Padiyar A. et al., International Journal of Advanced Pharmaceutics, 2016, 6 (2), 78-84, discloses a mixed solvency concept using solid solublizers for preparing injectable composition comprising diclofenac sodium in concentration 75 mg with a low volume of injection to 1 mL.

International Publication No. (PCT) WO 2016/170401 discloses injectable composition comprising diclofenac or water soluble salts thereof, in a solvent system containing water and two or more solubilizers, and optionally, one or more antioxidant (s) and/or one or more buffering agent (s) for administration via intradeltoid along with intragluteal, subcutaneous and slow intravenous route.

There still exists a need for a storage stable solution which enables safe and efficacious administration of concentrated solution of diclofenac without or with minimal pain.

SUMMARY OF THE INVENTION

In one general aspect, the present invention provides a stable, aqueous, injectable solution comprising diclofenac and polyvinylpyrrolidone (PVP).

In another general aspect, the present invention provides a process for preparing the injectable solution comprising diclofenac and polyvinylpyrrolidone.

In another general aspect, the present invention provides a method for treatment or management of pain and inflammation by administering the injectable solution of the present invention to the individual in need thereof.

The details of one or more embodiments of the invention are set forth in the description below. Other features, objects and advantages of the invention will be apparent from the description.

DETAILED DESCRIPTION OF THE INVENTION

The present invention provides a stable, aqueous, injectable solution comprising diclofenac and one or more pharmaceutically acceptable excipients.

The aqueous injectable solution may be in the form of a clear solution comprising diclofenac and polyvinylpyrrolidone.

The term "diclofenac" as used herein, unless and otherwise specifically mentioned, encompasses diclofenac base as well as its pharmaceutically acceptable salts, for example diclofenac sodium, diclofenac potassium, diclofenac diethanolamine etc.

The storage stable aqueous injectable solution may be administered via parenteral route, for example, intradeltoid, intragluteal, IV infusion or IV bolus route.

The term "about" as used herein, refers to encompass +/−20%, 15%, 10%, 5%, 2%, 1%, 0.5%, or 0.25% of the numerical value of the number with which it is being used.

The term "storage stable" as used herein, refers to any composition comprising a drug having sufficient physical and chemical stability to allow storage at a convenient temperature, such as between about 0° C. and about 40° C., for a commercially reasonable period of time. The term "physical stability" refers to maintenance of color or colorless state, dissolved oxygen level, head space oxygen level, and particulate matter size. The term "chemical stability" relates to formation of drug-related impurities in terms of total impurities, known impurities and single maximum unknown impurity, up to allowed limits by the Regulatory Agency. For pharmaceutical products, stability is required for commercially relevant times after manufacturing, such as for about 1, 3, 6, 12, 18, 24 or 36 months, during which a product is kept in its original packaging under specified storage conditions. The term composition includes the solution prepared in accordance with the present invention.

The term "controlled room temperature" as used herein, refers to the temperature between 20° C. and 25° C.

In one embodiment, the present invention provides a stable injectable solution comprising diclofenac, polyvinylpyrrolidone and water.

In another embodiment, the present invention provides a stable aqueous injectable solution comprising diclofenac and polyvinylpyrrolidone.

The stable aqueous injectable solution may comprise diclofenac sodium in a concentration of between about 10 mg/mL and about 500 mg/mL, for example, about 20 mg/mL, about 25 mg/mL, about 30 mg/mL, about 37.5 mg/mL, about 40 mg/mL, about 50 mg/mL, about 60 mg/mL, about 70 mg/mL, about 75 mg/mL, about 80 mg/mL, about 90 mg/mL, about 100 mg/mL, about 125 mg/mL, about 150 mg/mL, about 175 mg/mL, about 200 mg/mL, about 250 mg/mL, about 275 mg/mL, about 300 mg/m L, about 325 mg/mL, about 350 mg/mL, about 375 mg/mL, about 400 mg/mL, about 425 mg/mL, about 450 mg/mL, about 475 mg/mL or about 500 mg/mL.

The stable aqueous injectable solution may comprise polyvinylpyrrolidone in a concentration of between about 50 mg/mL and about 300 mg/mL, for example, about 60 mg/mL, about 70 mg/mL, about 80 mg/mL, about 100 mg/mL, about 120 mg/mL, about 140 mg/mL, about 160 mg/mL, about 180 mg/mL, about 200 mg/mL, about 220 mg/mL, about 250 mg/mL or about 280 mg/mL.

In another embodiment, the stable aqueous injectable solution may comprise diclofenac in a concentration of 25 mg/mL, 37.5 mg/mL or 75 mg/mL, wherein upon dilution of the solution with appropriate amount of the DSNS (solution of 5 percent dextrose in saline (0.9% sodium chloride)) or saline solution (0.9% sodium chloride), it may provide a diluted solution for parenteral administration having diclofenac concentration of 0.75 mg/mL, 0.30 mg/mL or 0.15 mg/mL, which remains clear (free of any crystals) after storage for 24 hours at controlled room temperature or at 2-8° C.

The stable aqueous injectable solution may have improved physical and chemical stability as per the specifications mentioned herein.

In one embodiment, the present invention provides a storage stable aqueous injectable solution comprising diclofenac and one or more pharmaceutically acceptable excipients, wherein the solution retains at least 95% of the diclofenac.

The storage stable aqueous injectable solution may retain at least 95% of the diclofenac sodium (% assay) after storage for at least 1 month, for example, 2 months, 3 months, 6 months, 12 months, 18 months of 24 months at controlled room temperature (CRT).

The storage stable aqueous injectable solution may retain at least 95% of the diclofenac sodium (% assay) after storage for at least 1 month, for example, 2 months, 3 months, 6 months, 12 months, 18 months of 24 months at 25° C. temperature and 60% relative humidity (% RH).

The storage stable aqueous injectable solution may retain at least 95% of the diclofenac sodium (% assay) after storage for at least 1 month, for example, 2 months, 3 months, 6 months, 12 months, 18 months of 24 months at 40° C. temperature and 75% RH.

In another embodiment, the stable aqueous injectable solution comprising diclofenac is clear (free of any crystals) by visual inspection. The solution may provide the value of absorbance not more than 1, for example, not more then 0.75, 0.5, 0.4, 0.3, 0.2, 0.1 or 0.05. The solution may provide the value of % transmittance not less than 90%, for example, not less than 95%, 96%, 97%, 98%, 99%, 99.5% or 99.9%.

In another embodiment, the stable aqueous injectable solution comprising diclofenac does not contain impurity A (1-(2,6-dichlorophenyl) indolin-2-one) more than 0.3%, for example, 0.2%, 0.1% or 0.05%, by weight of diclofenac, as measured by HPLC.

In another embodiment, the stable aqueous injectable solution comprising diclofenac and one or more pharmaceutically acceptable excipients does not contain impurity A (1-(2,6-dichlorophenyl) indolin-2-one) more than 0.3% by weight of diclofenac, as measured by HPLC.

In another embodiment, the stable aqueous injectable solution comprising diclofenac may have viscosity value between about 1.5 cP and 7.5 cP, for example, 2 cP, 2.5 cP, 3 cP, 3.5 cP, 4 cP, 4.5 cP, 5 cP, 5.5 cP, 6 cP, 6.5 cP or 7 cP.

In another embodiment, the stable aqueous injectable solution comprising diclofenac may have osmolality value between about 200 mOsm and about 600 mOsm, for example, about 250 mOsm, about 300 mOsm, about 350 mOsm, about 400 mOsm, about 450 mOsm, about 500 mOsm or about 550 mOsm.

In another embodiment, the stable aqueous injectable solution comprising diclofenac may have pH between about 7 and about 10, for example, about 7.5, about 8, about 8.5, about 9 or about 9.5.

The suitable pharmaceutically acceptable excipients for the solution of the present invention may include one or more pharmaceutically acceptable solvents, solubilizers, stabilizers, preservatives, antioxidants, surfactants, buffering agents, nucleation inhibitors, pH adjusting agents and isotonicity adjusting agents.

Examples of suitable pharmaceutically acceptable solvents may include, but not limited to, water for injection, and the like.

Examples of suitable pharmaceutically acceptable solubilizers may include, but not limited to benzyl benzoate, castor oil, cottonseed oil, N, N dimethylacetamide, dehydrated ethanol, glycerol, N-methyl-2-pyrrolidone, diethanolamine, L-arginine, peanut oil, poppyseed oil, safflower oil, sesame oil, soybean oil, vegetable oil, or any combination thereof.

Examples of suitable pharmaceutically acceptable stabilizers may include may include, but not limited to aminoethyl sulfonic acid, L-arginine, butylhydroxyanisol, Polyvinylpyrrolidone, L-cysteine, cysteine hydrochloride, diethanolamine, diethylenetriaminepentaacetic acid, ferric chloride, inositol, D,L-methionine, or any combination thereof.

Examples of suitable pharmaceutically acceptable preservatives may include, but not limited to, chlorobutanol, benzalkonium chloride, methyl paraben, propyl paraben, benzoic acid, sodium benzoate, sorbic acid, benzethonium chloride, cetyl pyridinium chloride, benzyl bromide, benzyl alcohol, phenylmercury nitrate, phenylmercury acetate, thiomersal, merthiolate, chlorhexidine, phenylethyl alcohol, quaternary ammonium chloride, sodium benzoate, sodium propionate, or any combination thereof.

Examples of suitable pharmaceutically acceptable antioxidants may include, but not limited to, butylated hydroxytoluene (BHT), butylated hydroxyanisole (BHA), propyl gallate, monothioglycerol, ascorbic acid, sodium ascorbate, erythorbic acid, potassium metabisulfite, sodium metabisulfit, propionic acid, sodium formaldehyde sulphoxylate, reduced glutathione, thiourea, cysteine, n-acetylcysteine, methionine, sodium sulfite, sodium bisulfate, alkyl gallate, including propyl gallate, vitamin E, or other tocopherol analogs, including tocopherol acetate or TPGS, or any combination thereof.

The stable aqueous injectable solution of the present invention may comprise monothioglycerol in a concentration of between about 1 mg/mL and about 10 mg/mL, for example, about 2 mg/mL, about 4 mg/mL, about 5 mg/mL, about 6 mg/mL or about 8 mg/mL.

Examples of suitable pharmaceutically acceptable surfactants may include, but not limited to, amphoteric, non-ionic, cationic or anionic molecules. Suitable surfactants may include, but not limited to, polysorbates 80 (e.g. tween 80 etc.), poloxamer (poloxamer 188), sodium lauryl sulfate, lauryl dimethyl amine oxide, docusate sodium, cetyl trimethyl ammonium bromide (CTAB), polyvinyl alcohol, polyethoxylated alcohols, polyoxyethylene sorbitan, octoxynol, polyoxyl lauryl ether, Brij® surfactants (polyoxyethylene vegetable-based fatty ethers derived from lauryl, cetyl, stearyl and oleyl alcohols), bile salts (such as sodium deoxycholate and sodium cholate), polyoxyl castor oil, nonylphenol ethoxylate, lecithin, polyoxyethylene surfactants, phospholipids such as dimyristoylphosphatidyl glycerol (DMPG), disteroylphosphatidylethanolamine (DSPE), 1,2-Distearoyl-phosphatidylethanolamine-methyl-polyethyleneglycol conjugate (DSPE-mPEG), monoalkanolamine condensates, polyoxyethylene fatty acid amides, quaternary ammonium salts, polyoxyethylene alkyl and alicyclic amines, polyoxyethylene, sorbitan monolaurate and stearate, Solutol® (ethylene oxide/12-hydroxy stearic acid), tyloxapol, or any combination thereof.

The stable aqueous injectable solution of the present invention may comprise polysorbate 80 in a concentration of between about 1 mg/mL and about 100 mg/mL, for example, about 2 mg/mL, about 5 mg/mL, about 7 mg/mL, about 10 mg/mL, about 20 mg/mL, about 40 mg/mL, about 50 mg/mL, about 60 mg/mL or about 80 mg/mL.

Examples of suitable pharmaceutically acceptable buffering agents may include, but not limited to, acetate (e.g. sodium acetate etc.), citrate (e.g. citric acid/sodium citrate etc.), phosphate (e.g. monobasic sodium phosphate, dibasic sodium phosphate etc.), carbonate, or any combination thereof.

Examples of suitable pharmaceutically acceptable nucleation inhibitors may include, but not limited to, polyvinylpyrrolidone, crospovidone, hydroxypropylmethyl cellulose (HPMC), poloxamers, polysorbate, phospholipids such as dimyristoylphosphatidyl glycerol (DMPG), disteroylphosphatidylethanolamine (DSPE), 1,2-Distearoyl-phosphatidylethanolamine-methyl-polyethyleneglycol conjugate (DSPE-mPEG), or any combination thereof. In one embodiment, polyvinylpyrrolidone may be PVP K12, PVP K17, PVP K25, PVP K30, PVPK 40 or PVP K90.

Examples of suitable pharmaceutically acceptable pH adjusting agents may include, but not limited to, sodium hydroxide, hydrochloric acid, boric acid, citric acid, acetic acid, phosphoric acid, succinic acid, potassium hydroxide, ammonium hydroxide, magnesium oxide, calcium carbonate, magnesium carbonate, malic acid, potassium citrate, sodium phosphate, lactic acid, gluconic acid, tartaric acid, fumaric acid, diethanolamine, monoethanolamine, sodium carbonate, sodium bicarbonate, triethanolamine, or any combination thereof. The stable aqueous injectable solution may comprise one or more pH adjusting agents in an amount to provide pH of the solution between about 8 and about 9, for example about 8.5.

Examples of suitable pharmaceutically acceptable isotonicity adjusting agents may include, but not limited to, sodium chloride, potassium chloride, calcium chloride, magnesium chloride, glucose, sucrose, dextrose, mannitol, glycerol, or any combination thereof.

The stable aqueous injectable solution of the present invention may comprise sodium chloride in a concentration of between about 1 mg/mL and about 5 mg/mL, for example, about 2 mg/mL, about 3 mg/mL or about 4 mg/mL.

In another embodiment, the stable injectable solution may comprise about 75 mg/mL of diclofenac, about 200 mg/mL of polyvinylpyrrolidone, about 20 mg/mL of polysorbate 80, about 5 mg/mL of monothioglycerol, one or more pH adjusting agents, for example, NaOH and/or HCl in a quantity sufficient to adjust pH of the solution about 8.5 and quantity sufficient water.

In another embodiment, the stable injectable solution may comprise about 75 mg/mL of diclofenac, about 150 mg/mL of polyvinylpyrrolidone, about 20 mg/mL of polysorbate 80, about 5 mg/mL of monothioglycerol, one or more pH adjusting agents, for example, NaOH and/or HCl in a quantity sufficient to adjust pH of the solution about 8.5 and quantity sufficient water.

In another embodiment, the stable injectable solution may comprise about 75 mg/mL of diclofenac, about 160 mg/mL of polyvinylpyrrolidone, about 20 mg/mL of polysorbate 80, about 5 mg/mL of monothioglycerol, one or more pH adjusting agents, for example, NaOH and/or HCl in a quantity sufficient to adjust pH of the solution about 8.5 and quantity sufficient water.

In another embodiment, the stable injectable solution may comprise about 25 mg/mL of diclofenac, about 70 mg/mL of polyvinylpyrrolidone, about 7 mg/mL of polysorbate 80, about 5 mg/mL of monothioglycerol, about 3 mg/mL of sodium chloride, one or more pH adjusting agents, for example, NaOH and/or HCl in a quantity to adjust pH of the solution about 8.5 and quantity sufficient water.

In another embodiment, the stable injectable solution may comprise about 37.5 mg/mL of diclofenac, about 80 mg/mL of polyvinylpyrrolidone, about 10 mg/mL of polysorbate 80, about 5 mg/mL of monothioglycerol, about 2 mg/mL of sodium chloride, one or more pH adjusting agents, for example, NaOH and/or HCl in a quantity to adjust pH of the solution about 8.5 and quantity sufficient water.

In another embodiment, the present invention provides a stable injectable solution comprising diclofenac and water, wherein the solution does not comprise any organic co-solvent.

The stable aqueous injectable solution does not comprise any toxic and/or irritant ingredient, for example, beta-cyclodextrin, transcutol, cremophor (polyethoxylated castor oil), glycofurol, propylene glycol and/or polyethylene glycol.

In another embodiment, the stable aqueous injectable solution does not comprise any local anesthetic, for example, lidocaine, prilocaine, tetracaine, bupivacaine, mepivacaine and/or xylocaine.

In another embodiment, the present invention provides a process for preparing a stable injectable solution comprising diclofenac, polyvinylpyrrolidone, polysorbate 80, monothioglycerol and water. The process includes steps: (a) adding polyvinylpyrrolidone, polysorbate 80 and monothioglycerol into water to form a clear solution, (b) adding diclofenac into the solution prepared in step (a), and (c) adding pH adjusting agent like NaOH/HCl to have pH of the solution between about 8 and about 9. Additionally, the process may include adding an appropriate amount of NaCl at the step (a). The prepared solution may be subjected to a terminal sterilization process.

In another embodiment, the present invention provides a method for treatment or management of pain and/or inflammation by administering the stable injectable solution to the individual in need thereof. In another embodiment, the physical and chemical stability of the injectable solution of the present invention was studied at 25° C. temperature and 60% relative humidity (% RH) as well as at 40° C. temperature and 75% RH.

Abbreviations

ND: Not Detected.
NMT: Not More Than.
BQL: Below Quantitation Limit.
NLT: Not Less Than.
q.s.: Quantity Sufficient.

The present invention is illustrated by the following examples which are provided to be exemplary of the invention and do not limit the scope of the invention.

Example 1

TABLE 1

| Sr. no | Ingredients | Amount in mg |
|---|---|---|
| 1 | Diclofenac sodium | 1500 |
| 2 | Polyvinylpyrrolidone K12 | 4000 |
| 3 | Polysorbate 80 | 400 |
| 5 | Sodium hydroxide | q.s. to pH 8.5 |
| 6 | Monothioglycerol | 100 |
| 7 | Water for Injection | q.s. to 20 mL |

Process

All the ingredients were used in an amount mentioned in Table 1, for preparing diclofenac injection solution, batch size 20 mL.

Polyvinylpyrrolidone K12, polysorbate 80 and monothioglycerol were added into 16 mL of water for injection, stirred and dissolved completely at controlled room temperature. Diclofenac sodium was added to the above prepared solution with moderate stirring at controlled room temperature. Then pH of the solution was adjusted to 8.5 using 5% w/v NaOH and/or 5% w/v HCl and the volume was made up to 20 mL using water for injection. The solution was filtered through a 0.22μ filter and filled into an amber colored glass vial.

Example 2

TABLE 2

| Solution | Solution 2A | Solution 2B |
|---|---|---|
|  | Amount in mg | |
| Diclofenac sodium | 1500 | 1500 |
| Polyvinylpyrrolidone K12 | 3000 | — |
| Polysorbate 80 | 400 | 400 |
| Sodium hydroxide | q.s. to pH 8.5 | q.s. to pH 8.5 |
| Monothioglycerol | 100 | 100 |
| Water for Injection | q.s. to 20 mL | q.s. to 20 mL |

Process

The process for preparing example 2 is same as the process for preparing example 1, with the exception that solution 2A contains 150 mg/mL polyvinylpyrrolidone K12 and solution 2B does not contain polyvinylpyrrolidone K12.

The solution 2A and solution 2B were tested for their physical stability and chemical stability, and the results are reported in the Table 2A below.

TABLE 2A

| Storage condition | Physical stability | | | Chemical stability (Impurity A) | |
|---|---|---|---|---|---|
|  | Initial | 1 day/ 25° C. | 1day/ 2-8° C. | Initial | 1day/ 80° C. |
| Solution 2A | Clear solution | Clear solution | Clear solution | ND | 0.13% |
| Solution 2B | Unstable. Crystallization of diclofenac occurs within 2 minutes of preparing the solution. | — | — | ND | 0.35% |

It is evident from a comparison of the stability data for solution 2A and solution 2B, provided at the above Table 2A, that polyvinylpyrrolidone provides physical as well as chemical stability to diclofenac sodium in the liquid injection solution.

Example 3

TABLE 3

| Sr. no | Ingredients | mg/mL |
|---|---|---|
| 1 | Diclofenac sodium | 75 |
| 2 | Polyvinylpyrrolidone K12 | 160 |
| 3 | Polysorbate 80 | 20 |
| 4 | Sodium hydroxide | q.s. to pH 8.5 |
| 5 | Hydrochloric acid | q.s. to pH 8.5 |
| 6 | Monothioglycerol | 5 |
| 7 | Water for Injection | q.s. to 1 mL |

Process

All the ingredients were used in a concentration as mentioned in Table 3, for preparing diclofenac injection solution having a batch size 500 mL.

In measured quantity of water for injection, nitrogen was sparged until dissolved oxygen was at a level up to 2 ppm. Polyvinylpyrrolidone K12 was added into 350 mL (70% amount of total batch size) of nitrogen sparged water for injection and dissolved by stirring at room temperature. Monothioglycerol was added into the above prepared solution. Polysorbate 80 was added to the above prepared solution and dissolved by stirring. Diclofenac sodium was added to the above prepared solution and dissolved by stirring at room temperature. Then, pH of the solution was adjusted to 8.5 using 5% w/v NaOH and/or 5% w/v HCl, and the volume was made up to 1500 mL using nitrogen sparged water for injection. The solution was filtered through a 0.2μ sterile filter and filled into a clear glass ampoule under pre- and post-nitrogen flushing.

The solution of example 3 was tested for certain parameters, (i) at initial time point ($T_0$), (ii) after 3 months (3M) storage at 25° C. temperature and 60% RH as well as at 40° C. temperature and 75% RH, and (iii) after 6 months (6M) storage at 25° C. temperature and 60% RH as well as at 40° C. temperature and 75% RH. The results are reported in the Table 3A below.

TABLE 3A

| Storage condition | Parameter | Initial | 3M | 6M |
|---|---|---|---|---|
| 25° C./60% RH | Description | Clear solution | Clear solution | Clear solution |
| | Assay (%) | 101.900 | 102.300 | 102.700 |
| | Impurity A | ND | ND | BQL |
| | pH | 8.720 | 8.450 | 8.480 |
| | Absorbance | 0.057 | 0.140 | 0.180 |
| | % Transmittance | 100.000% | 99.900% | 99.700% |
| | Viscosity (cP) | 6.310 | — | 5.910 |
| | Osmolality (mOsm) | 485 | 445 | 438 |
| 40° C./75% RH | Description | Clear solution | Clear solution | Clear solution |
| | Assay (%) | 101.900 | 103.000 | 102.700 |
| | Impurity A | ND | 0.02% | 0.11% |
| | pH | 8.720 | 8.370 | 8.450 |
| | Absorbance | 0.057 | 0.417 | 0.502 |
| | % Transmittance | 100.000% | 98.100% | 99.700% |
| | Viscosity (cP) | 6.310 | — | 5.910 |
| | Osmolality (mOsm) | 485 | 450 | 446 |

Measurement of absorbance and transmittance was done by UV spectrophotometer.

Measurement of viscosity was done by brookfield viscometer, model DV2T.

Measurement of osmolality (mOsm) was done by osmometer.

Measurement of assay (%) was done by HPLC (high performance liquid chromatography).

The solution of example 3 was diluted using appropriate quantities of saline solution (0.9% sodium chloride) to achieve diluted solutions comprising diclofenac in a concentration of 0.75 mg/mL, 0.30 mg/mL, and 0.15 mg/mL. All three diluted solutions were tested for certain parameters (i) at initial time point ($T_0$), (ii) after 24 hours storage at controlled room temperature (25° C.±2° C.), and (iii) after 24 hours storage at 2-8° C. temperature. The results are reported in the Table 3B below.

TABLE 3B

| Diclofenac Na conc. (mg/mL) | Temperature | Description | pH $T_0$ | pH 24 hrs | Assay (%) $T_0$ | Assay (%) 24 hrs | Total Impurities $T_0$ | Total Impurities 24 hrs |
|---|---|---|---|---|---|---|---|---|
| 0.75 | CRT | Clear | 7.20 | 6.65 | 100.40 | 100.60 | BQL | BQL |
| 0.30 | CRT | Clear | 6.95 | 6.45 | 96.90 | 100.10 | 0.06 | 0.02 |
| 0.15 | CRT | Clear | 6.63 | 6.25 | 99.00 | 98.80 | ND | BQL |
| 0.75 | 2-8° C. | Clear | 7.20 | 6.50 | 100.50 | 101.10 | ND | BQL |
| 0.30 | 2-8° C. | Clear | 6.95 | 6.28 | 96.60 | 98.60 | BQL | BQL |
| 0.15 | 2-8° C. | Clear | 6.63 | 6.08 | 98.90 | 98.80 | BQL | BQL |

Example 4

TABLE 4

| Sr. no | Ingredients | mg/mL |
|---|---|---|
| 1 | Diclofenac sodium | 25 |
| 2 | Polyvinylpyrrolidone K12 | 70 |
| 3 | Polysorbate 80 | 7 |
| 4 | Sodium chloride | 3 |
| 5 | Sodium hydroxide | q.s. to pH 8.5 |
| 6 | Hydrochloric acid | q.s. to pH 8.5 |
| 7 | Monothioglycerol | 5 |
| 8 | Water for Injection | q.s. to 1 mL |

Process

All the ingredients were used in a concentration as mentioned in Table 4, for preparing diclofenac injection solution having a batch size 1400 mL. The process for preparing example 4 is same as the process for preparing example 3, with the exception that example 4 contains an additional step of addition of sodium chloride and dissolved by stirring, after addition of polysorbate 80 and before the addition of diclofenac sodium.

The solution of example 4 was tested for certain parameters, (i) at initial time point ($T_0$), (ii) after 3 months (3M) storage at 25° C. temperature and 60% RH as well as at 40° C. temperature and 75% RH, and (iii) after 6 months (6M) storage at 25° C. temperature and 60% RH as well as at 40° C. temperature and 75% RH. The results are reported in the Table 4A below.

TABLE 4A

| Storage condition | Parameter | Initial | 3M | 6M |
|---|---|---|---|---|
| 25° C./60% RH | Description | Clear solution | Clear solution | Clear solution |
| | Assay (%) | 102.900 | 103.100 | 102.400 |
| | Impurity A | ND | BQL | BQL |
| | pH | 8.770 | 8.420 | 8.560 |
| | Absorbance | 0.034 | 0.067 | 0.099 |
| | % Transmittance | 99.500% | 98.800% | 99.000% |
| | Viscosity (cp) | 1.79 | — | — |
| | Osmolality (mOsm) | 340 | 329 | 335 |
| 40° C./75% RH | Description | Clear solution | Clear solution | Clear solution |
| | Assay (%) | 102.900 | 101.800 | 100.700 |
| | Impurity A | ND | 0.060% | 0.280% |
| | pH | 8.770 | 8.460 | 8.580 |
| | Absorbance | 0.034 | 0.215 | 0.234 |
| | % Transmittance | 99.500% | 98.900% | 98.800% |
| | Viscosity (cP) | 1.790 | — | — |
| | Osmolality (mOsm) | 340 | 315 | 326 |

Example 5

TABLE 5

| Sr. no | Ingredients | mg/mL |
|---|---|---|
| 1 | Diclofenac sodium | 37.5 |
| 2 | Polyvinylpyrrolidone K12 | 80 |
| 3 | Polysorbate 80 | 10 |
| 4 | Sodium chloride | 2 |
| 5 | Sodium hydroxide | q.s. to pH 8.5 |
| 6 | Hydrochloric acid | q.s. to pH 8.5 |
| 7 | Monothioglycerol | 5 |
| 8 | Water for Injection | q.s. to 1 mL |

Process

All the ingredients were used in a concentration as mentioned in Table 5, for preparing diclofenac injection solution having a batch size 500 mL.

The process for preparing example 5 is same as the process for preparing example 4.

The solution of example 5 was tested for certain parameters, (i) at initial time point ($T_0$) and (ii) after 3 months (3M) storage at 25° C. temperature and 60% RH as well as at 40° C. temperature and 75% RH. The results are reported in the Table 5A below.

TABLE 5A

| Storage condition | Parameter | Initial | 3M |
|---|---|---|---|
| 25° C./60% RH | Description | Clear solution | Clear solution |
|  | Assay (%) | 103.200 | 103.900 |
|  | Impurity A | BQL | 0.010% |
|  | pH | 8.290 | 8.120 |
|  | Absorbance | 0.047 | 0.139 |
|  | % Transmittance | 99.700% | 99.500% |
|  | Viscosity (cP) | 2.080 | — |
|  | Osmolality (mOsm) | 334 | 322 |
| 40° C./75% RH | Description | Clear solution | Clear solution |
|  | Assay (%) | 103.200 | 101.500 |
|  | Impurity A | BQL | 0.090% |
|  | pH | 8.290 | 8.170 |
|  | Absorbance | 0.047 | 0.333 |
|  | % Transmittance | 99.700% | 99.700% |
|  | Viscosity (cP) | 2.080 | — |
|  | Osmolality (mOsm) | 334 | 324 |

It is evident from a comparison of the stability data for Example 3, Example 4 and Example 5, provided at the above Table 3A, Table 3B, Table 4A and Table 5A, that the diclofenac solution of the present invention remains physically and chemically stable initially as well as upon storage at various storage conditions.

While the present invention has been described in terms of its specific embodiments, certain modifications and equivalents will be apparent to those skilled in the art and are intended to be included within the scope of the present invention.

The invention claimed is:

1. A stable aqueous solution for parenteral administration, comprising diclofenac sodium in the range of 10 mg/ml-500 mg/ml, polyvinylpyrrolidone in the range of 50 mg/ml-300 mg/ml, polysorbate 80 in the range of 1 mg/ml-100 mg/ml, and monothioglycerol in the range of 1 mg/ml-10 mg/ml, the solution having a pH in the range of 7-10, wherein the solution does not contain impurity A (1-(2,6-dichlorophenyl) indolin-2-one) more than 0.3% by weight of diclofenac, as measured by HPLC, and wherein the solution retains at least 95% of the diclofenac, after 6 months of storage at 40° C. and 75% relative humidity.

2. A method for treatment of pain comprising administering an aqueous solution via parenteral route, having a pH in the range of 7-10, comprising diclofenac sodium in the range of 10 mg/ml-500 mg/ml, polyvinylpyrrolidone in the range of 50 mg/ml-300 mg/ml, polysorbate 80 in the range of 1 mg/ml-100 mg/ml, and monothioglycerol in the range of 1 mg/ml-10 mg/ml, wherein the solution has an osmolality value between about 250 mOsm and about 400 mOsm.

* * * * *